United States Patent [19]

Bundy

[11] 4,141,918
[45] Feb. 27, 1979

[54] 2-DECARBOXY-2-ALKYLCARBONYL-3,7-INTER-M-PHENYLENE-3-OXA-4,5,6-TRI-NOR-11-DEOXY-PGE$_1$COMPOUNDS

[75] Inventor: Gordon L. Bundy, Portage, Mich.

[73] Assignee: The Upjohn Company, Kalamazoo, Mich.

[21] Appl. No.: 925,265

[22] Filed: Jul. 17, 1978

Related U.S. Application Data

[62] Division of Ser. No. 888,695, Mar. 21, 1978, Pat. No. 4,123,463.

[51] Int. Cl.$^2$ ............................................. C07C 177/00
[52] U.S. Cl. ................................................. 260/590 C
[58] Field of Search ................................... 260/590 C

[56] References Cited

U.S. PATENT DOCUMENTS

| | | | |
|---|---|---|---|
| 3,931,296 | 1/1976 | Hayashi et al. | 260/514 D |
| 3,953,435 | 4/1976 | Hayashi et al. | 260/240 R |
| 4,066,751 | 1/1978 | Hayashi et al. | 424/180 |

OTHER PUBLICATIONS

Derwent Farmdoc CPI No. 93049x.

Primary Examiner—Gerald A. Schwartz
Attorney, Agent, or Firm—Robert A. Armitage

[57] ABSTRACT

The present invention provides novel prostaglandin analogs wherein the C-2 carboxyl is replaced by alkylcarbonyl, i.e., a C-2 ketone. These novel 2-decarboxy-2-alkylcarbonyl-PG-type compounds are disclosed as improved gastrointestinal cytoprotective agents, being devoid or substantially devoid of other prostaglandin-type effects (e.g., smooth muscle or cardiovascular).

29 Claims, No Drawings

2-DECARBOXY-2-ALKYLCARBONYL-3,7-INTER-M-PHENYLENE-3-OXA-4,5,6-TRINOR-11-DEOXY-PGE$_1$ COMPOUNDS

The present application is a divisional application of Ser. No. 888,695, filed Mar. 21, 1978, now Patent No. 4,123,463.

The present invention relates to prostaglandin analogs, for whcih the essential material constituting disclosure therefor is incorporated by reference here from U.S. Pat. No. 4,123,463.

I claim:

1. A prostaglandin analog of the formula

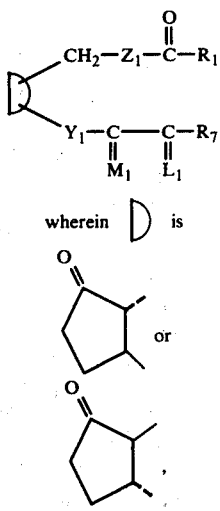

wherein 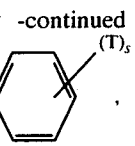 is

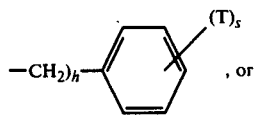

wherein R$_1$ is alkyl of one to 4 carbon atoms, inclusive;
wherein L$_1$ is wherein L$_1$ is

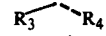 or
a mixture of

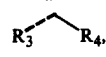
and

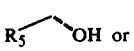

wherein R$_3$ and R$_4$ are hydrogen, methyl, or fluoro, being the same or different, with the proviso that one of R$_3$ and R$_4$ is methyl only when the other is hydrogen or methyl;
wherein M$_1$ is

 or

—(CH$_2$)$_m$—CH$_3$, wherein R$_5$ is hydrogen or methyl;
wherein R$_7$ is

—CH$_2$)$_h$— 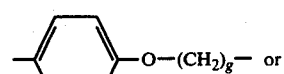 , or     (1)

—O— 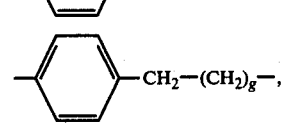    (3)

wherein h is zero to three, inclusive,
wherein m is one to 5, inclusive, s is zero, one, 2, or 3 and T is chloro, fluoro, trifluoromethyl, alkyl of one to 3 carbon atoms, or alkoxy of one to 3 carbon atoms, the various T's being the same or different, with the proviso that not more than two T's are other than alkyl;
wherein Y$_1$ is
(1) trans-CH=CH—
(2) cis-CH=CH—
(3) —CH$_2$CH$_2$—, or
(4) —C≡C—; and wherein Z$_1$ is —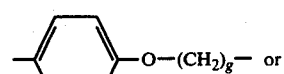—O—(CH$_2$)$_g$— or    (1)

—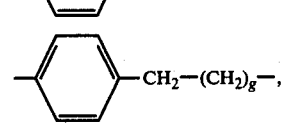—CH$_2$—(CH$_2$)$_g$—,    (2)

wherein g is one, two or three.

2. A prostaglandin analog according to claim 1, wherein R$_1$ is methyl.

3. A prostaglandin analog according to claim 2, wherein 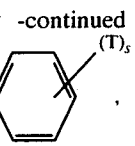 is

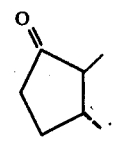

4. 2-Decarboxy-2-methylcarbonyl-3,7-inter-m-phenylene-3-oxa-4,5,6-trinor-11-deoxy-8β,12α-PGE$_2$, a prostaglandin analog according to claim 3.

5. A prostaglandin analog according to claim 2, wherein 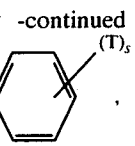 is

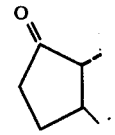

6. A prostaglandin analog according to claim 5, wherein Y$_1$ is cis-CH=CH-.

7. 2-Decarboxy-2-methylcarbonyl-3,7-inter-m-phenylene-3-oxa-4,5,6-trinor-13-cis-11-deoxy-PGE$_1$, a prostaglandin analog according to claim 6.

8. A prostaglandin analog according to claim 5, wherein Y$_1$ is —CH$_2$CH$_2$-.

9. 2-Decarboxy-2-methylcarbonyl-3,7-inter-m-phenylene-3-oxa-4,5,6-trinor-11-deoxy-PGE$_1$, a prostaglandin analog according to claim 8.

10. A prostaglandin analog according to claim 5, wherein Y$_1$ is -C≡C-.

11. 2-Decarboxy-2-methylcarbonyl-3,7-inter-m-phenylene-3-oxa-4,5,6-trinor-13,14-didehydro-11-deoxy-PGE$_1$, a prostaglandin analog according to claim 10.

12. A prostaglandin analog according to claim 5, wherein Y$_1$ is trans-CH≡CH-.

13. A prostaglandin analog according to claim 12, wherein R$_7$ is

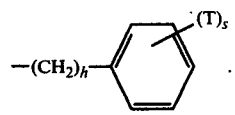

14. 2-Decarboxy-2-methylcarbonyl-3,7-inter-m-phenylene-3-oxa-4,5,6,18,19,20-hexanor-17-phenyl-11-deoxy-PGE$_1$, a prostaglandin analog according to claim 13.

15. A prostaglandin analog according to claim 12, wherein R$_7$ is

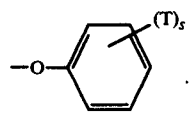

16. 2-Decarboxy-2-methylcarbonyl-3,7-inter-m-phenylene-3-oxa-4,5,6,17,18,-19,20-heptanor-16-phenoxy-11-deoxy-PGE$_1$, a prostaglandin analog according to claim 15.

17. A prostaglandin analog according to claim 12, wherein R$_7$ is -(CH$_2$)$_m$-CH$_3$-.

18. A prostaglandin analog according to claim 17, wherein Z$_1$ is

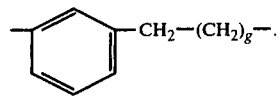

19. 2-Decarboxy-2-methylcarbonyl-3,7-inter-m-phenylene-4,5,6-trinor-11-deoxy-PGE$_1$, a prostaglandin analog according to claim 18.

20. A prostaglandin analog according to claim 17, wherein Z$_1$ is

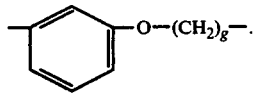

21. A prostaglandin analog according to claim 17, wherein R$_5$ is methyl.

22. 2-Decarboxy-2-methylcarbonyl-3,7-inter-m-phenylene-3-oxa-4,5,6-trinor-15-methyl-11-deoxy-PGE$_1$, a prostaglandin analog according to claim 17.

23. A prostaglandin analog according to claim 17, wherein R$_5$ is hydrogen.

24. A prostaglandin analog according to claim 23, wherein one of R$_3$ and R$_4$ is fluoro.

25. 2-Decarboxy-2-methylcarbonyl-3,7-inter-m-phenylene-3-oxa-4,5,6-trinor-16,16-difluoro-11-deoxy-PGE$_1$, a prostaglandin analog according to claim 24.

26. A prostaglandin analog according to claim 23, wherein at least one of R$_3$ and R$_4$ is methyl.

27. 2-Decarboxy-2-methylcarbonyl-3,7-inter-m-phenylene-3-oxa-4,5,6-trinor-16,16-dimethyl-11-deoxy-PGE$_1$, a prostaglandin analog according to claim 26.

28. A prostaglandin analog according to claim 23, wherein R$_3$ and R$_4$ are both hydrogen.

29. 2-Decarboxy-2-methylcarbonyl-3,7-inter-m-phenylene-3-oxa-4,5,6-trinor-11-deoxy-PGE$_1$, a prostaglandin analog according to claim 28.

* * * * *

UNITED STATES PATENT AND TRADEMARK OFFICE
CERTIFICATE OF CORRECTION

PATENT NO. : 4,141,918
DATED : February 27, 1979
INVENTOR(S) : Gordon L. Bundy

It is certified that error appears in the above-identified patent and that said Letters Patent are hereby corrected as shown below:

Column 1, lines 60-63 should read

-- wherein $R_5$ is hydrogen or methyl;

wherein $R_7$ is $-(CH_2)_m-CH_3,$  (1) -- instead of as it appears in the printed patent;

Column 2, line 19, "-C=C-;" should read -- $-C\equiv C-$; --; lines 20-30 should read as follows:

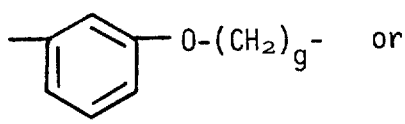

or

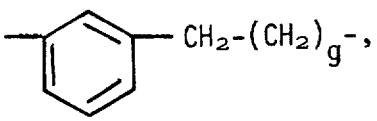

UNITED STATES PATENT AND TRADEMARK OFFICE
CERTIFICATE OF CORRECTION

PATENT NO. : 4,141,918
DATED : February 27, 1979
INVENTOR(S) : Gordon L. Bundy

It is certified that error appears in the above-identified patent and that said Letters Patent are hereby corrected as shown below:

Column 2, line 65, "11-deoxy-$PGE_1$," should read -- 9-deoxy-13,14-didehydro-$PGE_1$, --, Column 3, line 6, "-CH≡CH-" should read -- -CH=CH- --.

Signed and Sealed this

Eighteenth Day of September 1979

[SEAL]

Attest:

Attesting Officer

LUTRELLE F. PARKER
*Acting Commissioner of Patents and Trademarks*